United States Patent
Hirsch et al.

(10) Patent No.: US 6,197,302 B1
(45) Date of Patent: Mar. 6, 2001

(54) METHOD OF STIMULATING T CELLS

(75) Inventors: Raphael Hirsch, Cincinnati, OH (US); Constance M. Cullen, Florence, KY (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 08/914,421

(22) Filed: Aug. 19, 1997

Related U.S. Application Data

(62) Division of application No. 08/683,409, filed on Jul. 18, 1996.

(51) Int. Cl.[7] .................................................. A61K 39/385
(52) U.S. Cl. ....................................... 424/194.1; 424/193.1
(58) Field of Search .................................... 530/402, 807, 530/395; 424/193.1, 194.1

(56) References Cited

U.S. PATENT DOCUMENTS

| | | |
|---|---|---|
| 5,130,297 | 7/1992 | Sharma et al. . |
| 5,194,425 | 3/1993 | Sharma et al. . |
| 5,260,422 | 11/1993 | Clark et al. . |
| 5,284,935 | 2/1994 | Clark et al. . |
| 5,468,481 | 11/1995 | Sharma et al. . |
| 5,869,270 * | 2/1999 | Rhode et al. ........................ 435/7.24 |

FOREIGN PATENT DOCUMENTS

| | | |
|---|---|---|
| 352761 * | 1/1990 | (EP) . |
| WO 89/12459 | 12/1989 | (WO) . |
| WO 94/25054 | 11/1994 | (WO) . |
| WO 95/23814 * | 9/1995 | (WO) . |

OTHER PUBLICATIONS

"Expression and characterization of a class I MHC immunoglobulin heavy chain fusion protein." Cullen et al 9th International Congress of immunology: Abstract No. 2770, p. 468 San Francisco, Jul. 1995.

Dal Porto, J. et al. "A soluble divalent class I major histocompatibility complex molecule inhibits alloreactive T cells at nanomolar concentrations." *Proc. Natl. Acad. Sci. USA* (1993) vol. 90, pp. 6671–6675.

Buelow, R. et al. "Immunomodulation by Soluble HLA Class I." *Transplantation* (1995) vol. 59, pp. 649–654.

Nicolle, M. W. et al. "Specific Tolerance to an Acetylcholine Receptor Epitope Induced In Vitro in Myasthenia Gravis CD4+ Lymphocytes by Soluble Major Histocompatibility Complex Class II–Peptide Complexes." *J. Clin. Invest.* (1994) vol. 93, pp. 1361–1369.

Kozono, H. et al. "Production of soluble MHC class II proteins with covalently bound single peptides." *Nature* (1994) vol. 369, pp. 151–154.

Abastado, J–P. et al. "A soluble, single–chain $K^4$ molecule produced by yeast selects a peptide repertoire indistinguishable from that of cell–surface–associated $K^4$." *Eur. J. Immunol.* (1993) vol. 23, pp. 1776–1783.

Williams, M.E. et al. "Antigen Receptor–Mediated Anergy In Resting T Lymphocytes And T Cell Clones." *J. Immunol.* (1992) vol. 149, pp. 1921–1926.

Mage, M.G. et al. "A recombinant, soluble, single–chain class I major histocompatibility complex molecule with biological activity." *Proc. Natl. Acad. Sci, USA* (1992) vol. 89, pp. 10658–10662.

Arnold, B. et al. "Transgenic mice expressing a soluble foreign H–2 class I antigen are tolerant to allogeneic fragments presentedby self class I but not to the whole membrane–bound alloantigen." *Proc. Natl. Acad. Sci. USA* (1990) vol. 87, pp. 1762–1766.

Schneck, J. et al. "Inhibition of an Allospecific T Cell Hybridoma by Soluble Class I Proteins and Peptides: Estimation of the Affinity of a T Cell Receptor for MHC." *Cell* (1989) vol. 56, pp. 47–55.

Arnold, B. et al. "Alloreactive immune responses of transgenic mice expressing a foreign transplantation antigen in a soluble form." *Proc. Natl. Acad. Sci. USA* (1988) vol. 85, pp. 2269–2273.

McCluskey, J. et al. "T Cell Activation By Purified, Soluble, Class I MHC Molecules." *J. Immunol.* (1988) vol. 141, pp. 1451–1455.

Herrmann, S. H. and Mescher, M.F. "The Requirements for Antigen Multivalency In Class I Antigen Recognition and Triggering of Primed Precursor Cytolytic T Lymphocytes." *J. Immunol.* (1986) vol. 136, No. 8, pp. 2816–2825.

Herrmann, S.H. and Mescher, M. F., "Secondary cytolytic T lymphocyte stimulation by purified $H–2K^\kappa$ in liposomes." *Proc. Natl Acad. Sci. U.SA* (1981) vol. 78, pp. 2488–2492.

Kumar et al., P.N.A.S. USA, vol. 87:1337–1341 (1990).

Konig et al., J. Exp. Medicine, vol. 182 779–787 (1995).

Harding et al., J. Exp. Medicine, vol. 177:1791–1796 (1993).

Roit et al., Immunology, C.V. Mosby, Publishers, St. Louis, p. 5.3 (1986.

\* cited by examiner

*Primary Examiner*—Patrick J. Nolan
(74) *Attorney, Agent, or Firm*—Knobbe, Martens, Olsen & Bear, LLP

(57) ABSTRACT

The present invention describes a soluble fusion protein composed of a plurality of major histocompatibility complex (MHC) molecules linked together by a stabilizing structure herein referred to as the "linker," the MHC molecules being loaded with a specific peptide or peptides. Such fusion proteins can be used as a method for stimulating or inhibiting specific T cell clones expressing T cell receptors (TCR) restricted to the specific MHC-peptide combination. Such fusion proteins can thus be used as delivery systems to stimulate T cell immunity and as a treatment for diseases such as transplant rejection or autoimmunity.

3 Claims, 1 Drawing Sheet

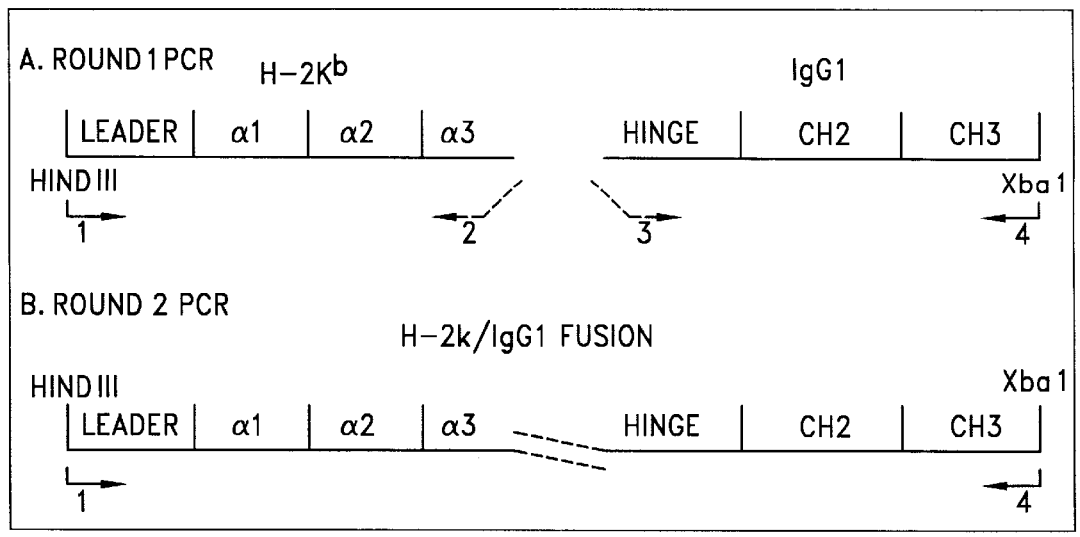
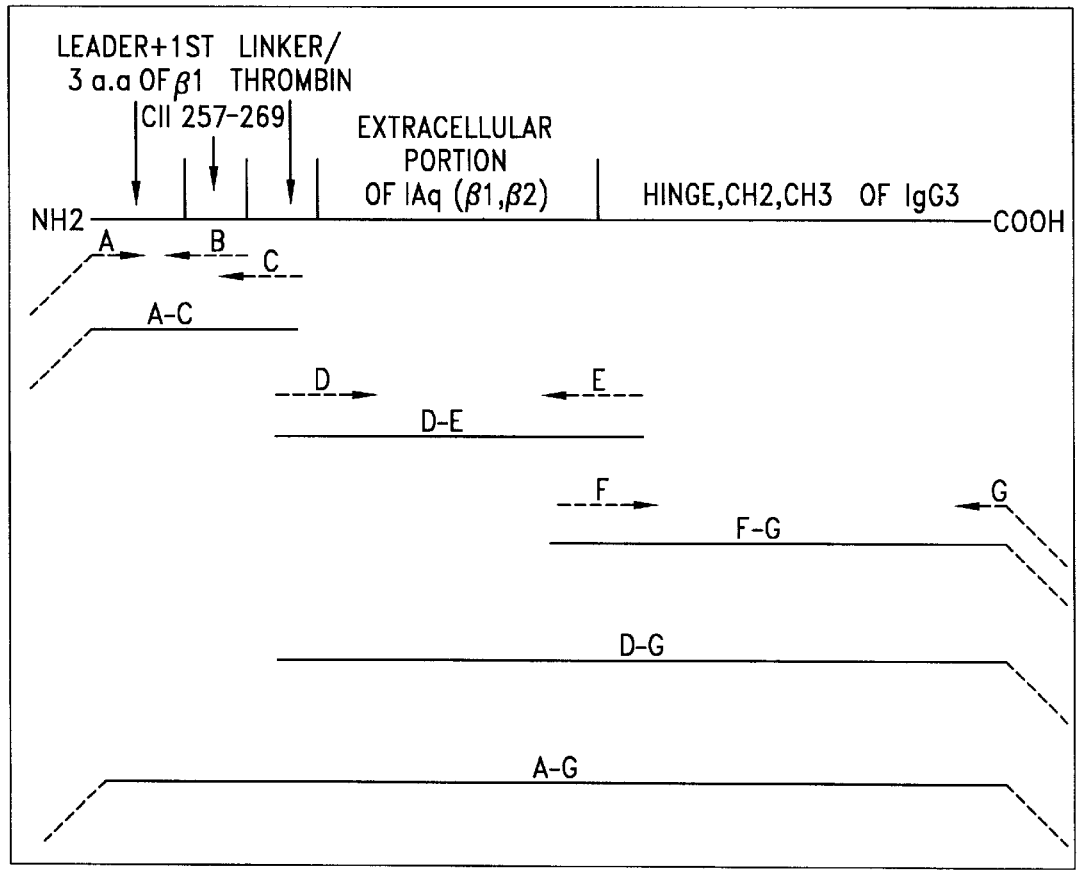
FIG. 1
FIG. 2

METHOD OF STIMULATING T CELLS

This application is a divisional of U.S. patent application Ser. No. 08/683,409, filed Jul. 18, 1996.

BACKGROUND OF THE INVENTION

T cells mediate many immune responses, including transplant rejection, autoimmunity, viral infections, and tumor surveillance. T cell recognition of peptide antigens occurs via the T cell receptor (TCR) and requires that such antigen be presented to the TCR by a major histocompatibility complex (MHC) molecule, generally situated on the surface of an antigen presenting cell. The peptide antigen is held by the MHC molecule such that the T cell receptor recognizes the unique structure formed by the combination of the MHC molecule and the specific peptide. Thus, only a small percentage of T cell clones react to a given peptide.

There are two major known types of MHC molecules: class I and class II. MHC class I molecules are composed of an alpha chain with 3 domains ($\alpha 1$, $\alpha 2$, and $\alpha 3$), as well as transmembrane and cytoplasmic domains. The $\alpha 1$ and $\alpha 2$ domains are polymorphic. A non-polymorphic protein, $\beta 2$-microglobulin, self associates with the alpha chain and is necessary for stable conformation. MHC class I molecules are widely distributed and are present on most nucleated cells.

MHC class II molecules are composed of an alpha chain and a beta chain that self associate to form a heterodimer. Each chain has two extracellular domains ($\alpha 1$, $\alpha 2$ and $\beta 1$, $\beta 2$), as well as transmembrane and intracellular domains. The $\alpha 1$ and $\beta 1$ domains are polymorphic. MHC class II molecules are more restricted in distribution than are class I molecules.

Polymorphisms in the MHC molecules, as well as the wide spectrum of unique peptides that can associate with the MHC, result in an extremely diverse recognition pattern such that a given MHC-peptide combination is only recognized by a small percentage of T cell clones.

Present methods for modulating T cell function suffer from a number of limitations including lack of specificity. For example, therapies for suppressing T cell function (such as in autoimmunity or transplant rejection) cause generalized immunosuppression and may leave patients at risk for developing life-threatening infections. The ultimate goal of anti-T cell immunosuppressive therapy is to inhibit specific T cell alloreactive or autoreactive clones while leaving the majority of T cells fully functional. Specific immunosuppressive therapy requires targeting T cell clones recognizing specific MHC/peptide combinations. Several researchers have attempted to use soluble class I MHC molecules to inhibit allogenic T cell responses in vitro or in vivo. In general, soluble class I molecules have not effectively inhibited alloreactive T cell responses. Failure to observe inhibition of T cell function with soluble MHC may relate to the requirement for divalency to induce T cell anergy.

Present therapies for enhancing T cell function (such as in certain infections and malignancies) are often insufficient to induce an adequate immune response. Immunization with peptides alone has often not been successful at inducing a sufficient T cell response, since the peptide is quickly degraded by peptidases.

Several reports indicate that divalency of the MHC molecules is critical for signal delivery to the T cell, including both activating and inhibitory signals. Further, T cell priming requires stimulation via the TCR and an additional second signal generally delivered by an antigen presenting cell. In the absence of a second signal, T cell hyporesponsiveness results.

SUMMARY OF THE INVENTION

The present invention includes the process of creating a fusion protein that modulates T cell function in a peptide-specific manner, and the various methods by which the fusion protein modulates such function. The present invention is premised on the realization that a fusion protein which modulates specific T cell activity consists of three parts: (1) a plurality of MHC molecules; (2) a linker connecting the MHC molecules; and (3) a specific peptide or peptides loaded into the MHC molecules. In particular, the invention is directed to a fusion protein comprising a plurality of MHC molecules complexed to both a linker and to a selected peptide. The fusion protein targets the T cell receptor and modulates T cell function. Methods of stimulating, inhibiting or destroying T cells are provided by the fusion proteins. By constructing a fusion protein in which the linker allows delivery of a second signal, T cell stimulation results in enhanced T cell immunity. By constructing a fusion protein in which the linker does not provide for delivery of a second signal, T cell suppression results in immunosuppression. The fusion proteins can be delivered in vivo as superior therapeutic agents for T cell-mediated processes such as autoimmunity, infections, malignancies, and transplantation rejection.

The objects and advantages of the present invention will be further appreciated in light of the following detailed description and drawings in which:

BRIEF DESCRIPTION OF THE DRAWINGS

FIG. 1 is a schematic representation of the PCR reactions used to form an MHC I IgG fusion protein.

FIG. 2 is a schematic representation of the PCR reactions used to form an MHC II IgG fusion protein.

DETAILED DESCRIPTION

The present invention includes the process of creating a fusion protein that modulates T cell function in a peptide-specific manner, and the various methods by which the fusion protein modulates such function. The present invention is premised on the realization that a fusion protein which modulates specific T cell activity consists of three parts: (1) a plurality of MHC molecules; (2) a linker connecting the MHC molecules; and (3) a specific peptide or peptides loaded into the MHC molecules. In particular, the invention is directed to a fusion protein comprising a plurality of MHC molecules complexed to both a linker and to a selected peptide. The fusion protein targets the T cell receptor and modulates T cell function. Methods of stimulating inhibiting or destroying T cells are provided by the fusion proteins.

The MHC molecules of the fusion protein can be either MHC class I or MHC class II and can consist of the entire MHC chains, the extracellular portions of the chains, the peptide binding portion of the chains, or any other suitable fragment of MHC. Exemplary human MHC molecules include HLA-A, HLA-B, HLA-C, DP, DQ and DR. Bivalency or multivalency of the MHC molecules is critical for signal delivery (either activation or inhibition signals) to the T cell. Therefore, the fusion protein of the present invention includes at least two identical MHC molecules attached to a linker.

The linker of the fusion protein serves three functions. First, the linker contributes the required bivalency or multivalency. Second, the linker increases the half-life of the entire fusion protein in vivo. Third, the linker determines whether the fusion protein will activate or suppress T cells. T cell priming requires stimulation via the TCR and an additional second signal generally delivered by the antigen presenting cell. In the absence of a second signal, T cell hyporesponsiveness results. By constructing a fusion protein in which the linker allows delivery of a second signal, T cell stimulation results in enhanced T cell immunity. By constructing a fusion protein in which the linker does not provide for delivery of a second signal, T cell suppression results in immunosuppression.

A fusion protein with T cell stimulatory properties can be constructed by using a linker which allows for delivery of a second signal to the T cell in addition to the signal delivered via the TCR. This can be accomplished by using a linker that has binding affinity for a cell surface structure on another cell, that cell being capable of delivering a second signal to the T cell. Thus, the linker serves to bridge the T cell and the other cell. By bringing the other cell into close proximity to the T cell, the other cell can deliver a second signal to the T cell. Examples include linkers that can bind to Fc receptors on other cells such as certain immunoglobulin chains or portions of immunoglobulin chains. Specific examples include IgG, IgA, IgD, IgE, and IgM. When an immunoglobulin is used, the entire protein is not required. For example, the immunoglobulin gene can be cleaved at the hinge region and only the gene encoding the hinge, CH2, and CH3 domains of the heavy chain is used to form the fusion protein. The linker may bind other cell surface structures. For example, the linker can include a cognate moiety for many cell surface antigens which can serve as a bridge to bring the second cell into close proximity with the T cell. The linker might also deliver a second signal independently. For example, a linker with binding affinity for the T cell antigen CD28 can deliver a second signal. Thus the linker contributes the required bivalency or multivalency and determines whether the fusion protein will serve to enhance or suppress T cell function. In addition, the linker can increase the half-life of the entire fusion protein in vivo.

A fusion protein with T cell inhibitory properties can be constructed by using a linker that does not result in delivery of a second signal. Examples include Ig chains that do not bind Fc receptor, Ig $F(ab')_2$ fragments, a zinc finger motif, a leucine zipper, and non-biological materials. Examples of non-biological materials include plastic microbeads, or even a larger plastic member such as a plastic rod or tube, as well as other physiologically acceptable carriers which are implantable in vivo.

The specific peptide of the fusion protein can be loaded into the MHC molecules after the fusion protein has been made. The peptide may also be subsequently covalently attached to the MHC, for example by UV cross-linking. Alternatively, a peptide sequence can be incorporated into the DNA sequence encoding the fusion protein such that the peptide is loaded into the MHC molecules during generation of the fusion protein. In the latter example, the peptide can be attached with a tether, such as polylysine, which allows it to complex with the MHC portion of the fusion protein.

The specific peptides to be loaded into the MHC molecules are virtually limitless and are determined based on the desired application. For example, to enhance T cell immunity to viral, fungal and bacterial infections, or to tumors, peptides from these sources can be used. To suppress T cell immunity in autoimmunity, autoreactive peptides can be used. To suppress T cell immunity to transplanted tissues, self peptides which are presented by alloantigen can be used.

Toxins, such as ricin and diphtheria toxin, and radioisotopes, may be complexed to the fusion protein (for example, using 5-methyl-2-iminothiolane) to kill the specific T cell clones. These toxins can be chemically coupled to the linker or to the MHC portion of the fusion protein, or they can be incorporated into the DNA sequence encoding the fusion protein such that the toxin is complexed to the fusion protein during generation of the fusion protein.

The fusion protein can be prepared by constructing a gene which encodes for the production of the fusion protein. Alternatively, the components of the fusion protein can be assembled using chemical methods of conjugation. Sources of the genes encoding the MHC molecules and the linkers can be obtained from DNA databases such as GenBank, as well as from published scientific literature in the public domain. In the case of MHC class I fusion proteins, the MHC fragment can be attached to the linker and β2 microglobulin can be allowed to self-associate. Alternatively, the fusion protein gene can be constructed such that β2 microglobulin is attached to the MHC fragment by a tether. In the case of MHC class II fusion protein, either the alpha or the beta chain can be attached to the linker and the other chain can be allowed to self-associate. Alternatively, the fusion protein gene can be constructed such that the alpha and beta chains are connected by a tether. Peptides can be prepared by encoding them into the fusion protein gene construct or, alternatively, with peptide synthesizers using standard methodologies available to one of ordinary skill in the art. The resultant complete fusion proteins can be administered by injection into the patient and can be repeated if necessary to provide a boosting reaction. Generally, the amount of fusion protein administered by injection for therapeutic purposes would range from about 1 μg to about 100 mg per kilogram body weight. With a solid linker, the fusion protein could be injected if microparticles are used, or physically implanted if a larger linker is used.

The construction and use of the fusion proteins of the present invention is further explained and demonstrated by the following detailed examples:

Example 1

Design of a Class I Fusion Protein

Design of a Divalent $K^b/IgG_1$

As shown in FIG. 1, constructs encoding the hinge, CH2 and CH3 regions of mouse $IgG_1$ heavy chain and the extracellular domains (α1, α2, and α3) of the MHC class I (H-2$K^b$) molecule were individually amplified using the polymerase chain reaction (PCR). Primers 1 and 2 were used to amplify the MHC class I fragment. Primers 3 and 4 were used to amplify the $IgG_1$ fragment. The 5' end of primer 2 has sequence homology to the 5' end of the hinge region of $IgG_1$. The 5' end of primer 3 has sequence homology to the 3' end of the α3 domain of $K^b$. The products were annealed in a subsequent PCR reaction using primers 1 and 4 to generate the fusion gene and amplified by another round of PCR. The sequences of the PCR primers were:

Primer 1: G C G C A T C G A T A T G G T A C C G T G C A C G C T G C T; (SEQ ID NO:1)

Primer 2: C C C T G G G C A C C C A T C T C A G G G T G A G G G G C; (SEQ ID NO:2)

Primer 3: C C T G A G A T G G G T G C C C A G G G A T T G T G G T; (SEQ ID NO:3)

Primer 4: A A G C A T T C T A G A T C A T T T A C C A G G A G A G T G. (SEQ ID NO:4)

The final product was digested with restriction enzymes and ligated into the expression vector pRcCMV, encoding the neomycin resistance gene. *Escherichia coli* strain DH5α was transformed and ampicillin resistant colonies were selected. DNA from transformed colonies was extracted and the entire fusion gene was sequenced. The fusion construct was transiently transfected into COS-7 cells using calcium phosphate precipitation. The plasmid pHuActβ2, encoding murine β2 microglobulin under the control of the human β actin promoter, was cotransfected. The resulting fusion protein was a soluble homodimer of 120 kd.

Stable transfectants were generated by electroporating (960 μF, 260 V, ∞ resistance) J558L cells (ATCC) with 10 μg of the fusion protein plasmid and 10 μg of pHuActβ2. For a negative control, cells were transfected with 10 μg of pRcCMV without insert. Cells were grown for 24 hours and neomycin resistant cultures were selected by growing the cells in 900 μg/ml G418.

Immunoprecipitation with Y3-sepharose. The monoclonal antibody Y3, which recognizes a conformational epitope of H-2K$^b$, was conjugated to sepharose and used to immunoprecipitate $^{35}$S-labeled supernatants from the stable transfectants. Immunoprecipitation with this monoclonal antibody yielded a 120 kDa homodimer, whereas negative control cell lines had no protein precipitated by this monoclonal antibody. This result indicated that the etitope recognized by Y3 is preserved in the fusion protein.

ELISAs. A Y3-based ELISA and an ELISA using a commercially available anti-H-2K$^b$ monoclonal antibody (recognizing an epitope distinct from Y3) was used to measure the presence of the fusion protein in supernatants derived from the stable transfectants. Supernatants from cells expressing the fusion protein construct were reactive with both of the H-2K$^b$-specific monoclonal antibodies whereas control supernatants showed no reactivity with these antibodies. The binding of Y3 to the fusion protein was increased by loading the fusion protein with a peptide known to bind efficiently to H-2K$^b$ (ovalbumin 257–264; ova). This result indicates that the fusion protein can be loaded with peptide which binds to H-2K$^b$ efficiently.

Activation of a T-hybridoma using immobilized fusion protein. The H-2K$^b$-restricted, ova-specific T-hybridoma B3.645, was cultured with fusion protein which was immobilized to polystyrene using an anti-IgG1 antibody. The fusion protein was loaded with either ova 257–264 or a control peptide (vesicular stomatitis virus nuclear protein 52–59; vsv), which is known to bind to H-2K$^b$. The T-hybridoma secreted interleukin 2 (IL-2) only in response to the fusion protein which was loaded with ova, but not the control VSV peptide. Control supernatant, containing ova without fusion protein, also did not induce IL-2 secretion. Further, the fusion protein loaded with ova was not able to induce IL-2 secretion from a T-hybridoma (2B4) restricted to another MHC molecule. These results indicate that the fusion protein was able to activate B3.645 through the TCR, and that activation was peptide specific and MHC restricted.

Activation of an H-2K$^b$ restricted, ova-specific cytotoxic T cell (CTL) using immobilized fusion protein. Immobilized, ova-loaded fusion protein was able to induce ova-specific H-2K$^b$ restricted CTL to secrete IL-3. In contrast, fusion protein loaded with vsv, or control supernatant containing ova alone, were not able to induce IL-3 secretion. This result shows that the fusion protein activates a T cell line, in addition to a T-hybridoma. Additionally, it shows that the fusion protein has biological effects on CTL.

T cell anergy induced by immobilized fusion protein. B3.645 cells were cultured with ova-loaded immobilized fusion protein for twenty-four hours. The cells were collected and rested for 3 days, at which time they were re-exposed to ova-loaded immobilized fusion protein. Measurements of IL-2 indicated that B3.645 cells which had received a primary stimulus of ova-loaded fusion protein were not able to respond to a subsequent stimulation with the ova-loaded fusion protein. In contrast, if the primary stimulus was VSV-loaded fusion protein, the B3.645 cells were able to respond to a secondary stimulation of ova-loaded fusion protein. The anergy induced in this cell line was not due to down-modulation of the TCR, as demonstrated by flow cytometry analysis. These results show that the fusion protein is able to induce anergy in a T-hybridoma in a peptide specific manner.

Soluble fusion protein inhibits secretion of IL-2 from B3.645 in response to ova-loaded antigen presenting cells: B3.645 cells incubated with antigen presenting cells (EL4) pulsed with the ova peptide produce IL-2. Ova-loaded fusion protein was able to inhibit the secretion of IL-2 from such ova-pulsed B3.645 T-hybridoma cells. This demonstrates that soluble fusion protein loaded with the appropriate peptide prevents the activation of the T-hybridoma.

Serum half life. One ml of ammonium sulfate concentrated culture supernatant-containing fusion protein was injected intraperitoneally into C57BL/10 mice. Mice were bled at various intervals and sera were tested by ELISA. No drop in titers was noted over a 2-week observation period, indicating that the fusion protein was stable in vivo.

Suppression of skin allograft rejection. C57BL/10 (H-2k$^b$) mice were treated with 1 ml of ammonium sulfate concentrated culture supernatant-containing fusion protein. A skin graft from a B6.C-H$^{bm1}$ donor (a congenic strain differing at the K locus) was then grafted. Skin graft rejection was delayed in mice treated with fusion protein, but not in controls.

Example 2

Design of a Class II Fusion Protein

Design of Divalent IA$^q$/IgG$_3$

Part I: Generation of soluble α-chain of IA$^q$

PCR was used to amplify the extracellular portion of the α-chain from a cDNA clone. The 5' primers were designed to incorporate either a Bgl II or a Pst I restriction site for subcloning into one of the pCMV expression vectors. The 3' primer was designed to incorporate a Sma I restriction site. Sequences of the primers were:

```
1. alpha 5' Bgl:  5' AAAGATCTAGGATGCCGCGCAGCAGA 3'  (SEQ ID NO:5)

2. alpha 5'Pst:   5' AACTGCAGAGGATGCCGCGCAGCAGA 3'  (SEQ ID NO:6)

3. alpha 3'Sma:   5' AACCCGGGTTAAGTCTCTGTCAGCTC 3'  (SEQ ID NO:7)
```

The cDNA was amplified with the primer sets: alpha 5' Bgl and alpha 3' Sma or alpha 5' Pst and alpha 3' Sma. The final PCR products were electrophoresed through 1% agarose gels, stained with ethidium bromide and the appropriate size bands (650 bp) were excised. The DNA was purified using the Gene Clean II Kit (BIO 101, Inc., Vista, Calif.) according to the manufacturer's instructions. Purified DNA was digested with the appropriate restriction enzymes (either Bgl II and Sma I or Pst I and Sma I) and then ligated into the expression vector pCMV4 which had been digested with Bgl II and Sma I or into pCMV8 which had been digested with Pst I and Sma I. The ligations were transformed into competent *Escherichia coli* strain JM109 and ampicillin resistant colonies were selected, DNA was prepared, and the entire gene was sequenced to ensure no spurious mutations were introduced during the PCR.

Part II: Generation of the IgG$_3$/β-chain Fusion Gene

As shown in FIG. 2, the fusion gene was generated through a series of nested and overlapping PCR reactions. Primers are designated A–G. Primers A and B were used to amplify a 150 base pair fragment from the α-chain of the IA$^q$ cDNA and incorporating a collagen II (CII) peptide. Primer A is homologous to the leader sequence of the β-chain and encodes a Sal I restriction site to facilitate subcloning of the final PCR product into the pCMV8 expression vector. Primer B has homology to the sequence encoding the first three amino acids of the β1 domain of the β-chain and a region of non-homology to encode the CII peptide (amino acids 257–269, CII 257–269). The PCR product from this reaction was purified as described for the α-chain and re-amplified with primer A and primer C. Primer C has homology to the 3' region of the A–B PCR product plus a sequence of non-homology encoding the rest of CII 257–269 and part of a linker and thrombin cleavage site. This reaction generated the A–C PCR product. In a separate reaction, primers D and E were used to amplify the extracellular portion (β1 and β2 domains) from the IA$^q$ cDNA. Primer D has homology to the β1 domain and to the 3' end of the A–C PCR product. Primer E has homology to the end of the β2 domain and a region of non-homology corresponding to the hinge region of IgG$_3$. This PCR product (D–E) was gel purified as described. To generate the F–G PCR product, cDNA was prepared from a murine plasma cell known to produce an immunoglobulin of the IgG$_3$ subclass (BP107.2.2, ATCC). Total RNA was made using RNazol (Teltest Inc., Friendsworth, Tex.) according to the manufacturer's directions. Oligo dT was used to prime the cDNA reaction using the Superscript Preamplification System (Gibco BRL, Gaithersburg, Md.) according to the manufacturer's directions. One twentieth of the cDNA reaction was amplified with primers F and G to generate a PCR fragment (F–G) encoding the hinge, CH2 and CH3 domains of the IgG$_3$ molecule. Primer F has homology to the hinge region of IgG$_3$ and homology to the 3' region of the D–E PCR product. Primer H has homology to the CH3 domain and encodes an Sma I restriction site for subcloning the final PCR product into the expression vector. The F–G PCR product was purified and amplified together with the D–E PCR product using primers D and G to generate the PCR product D–G. This product was purified on a gel, and annealed with the A–C PCR product using primers A and G. The final 1500 base pair fragment was purified on a gel, digested with Sal I and Sma I and ligated into the pCMV8 expression vector as described for the α-chain. The sequences of the primers are:

```
A.  5' CBGTCGACGGATGGCTCTGCAGAT 3'                                         (SEQ ID NO:8)

B.  5' GGGGCCTTGTTCGCCTTTGAAGCCAGCAATACCCAGCTCGGAGTTTCCGCCCTC 3'           (SEQ ID NO:9)

C.  5' GCCCCGTGGCAGTAGTGAGCCACCACCTCCGGGGCCTTGTTCGCC 3'                    (SEQ ID NO:10)

D.  5' GAACAAGGCCCCGGAGGTGGTGGCTCACTAGTGCCACGGGGCTCT 3'                    (SEQ ID NO:11)

E.  GTATTCTAGGCTTGCTCCGGGCAGA 3'                                           (SEQ ID NO:12)

F.  TCACTGTGGAGTGGAGGGCACAGTCCGAGTCTGCCCGGAGCAAGC 3'                       (SEQ ID NO:13)

G.  TTCCCGGGTCATTTACCAGGGGAGCG 3'                                          (SEQ ID NO:14)
```

As shown by the preceding description and examples, the fusion protein of the present invention can be used in a variety of different applications, both in suppression of T cell functions and enhancement of T cell functions. The specificity of the present invention is particularly useful since the fusion protein is loaded or complexed to a peptide which, together with the MHC, recognizes T cell clones bearing specific TCR.

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO: 1:

GCGCATCGAT ATGGTACCGT GCACGCTGCT                                    30

(2) INFORMATION FOR SEQ ID NO: 2:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (xi) SEQUENCE DESCRIPTION: SEQ ID NO: 2:

CCCTGGGCAC CCATCTCAGG GTGAGGGGC                                     29

(2) INFORMATION FOR SEQ ID NO: 3:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO: 3:

CCTGAGATGG GTGCCCAGGG ATTGTGGT                                      28

(2) INFORMATION FOR SEQ ID NO: 4:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO: 4:

AAGCATTCTA GATCATTTAC CAGGAGAGTG                                    30

(2) INFORMATION FOR SEQ ID NO: 5:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO: 5:

AAAGATCTAG GATGCCGCGC AGCAGA                                        26

(2) INFORMATION FOR SEQ ID NO: 6:

(i) SEQUENCE CHARACTERISTICS:
       (A) LENGTH: 26 base pairs
       (B) TYPE: nucleic acid
       (C) STRANDEDNESS: single (D) TOPOLOGY: linear (xi) SEQUENCE DESCRIPTION: SEQ ID NO: 6:

AACTGCAGAG GATGCCGCGC AGCAGA                                                26

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 7:

AACCCGGGTT AAGTCTCTGT CAGCTC                                                26

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 8:

CBGTCGACGG ATGGCTCTGC AGAT                                                  24

(2) INFORMATION FOR SEQ ID NO: 9:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 9:

GGGGCCTTGT TCGCCTTTGA AGCCAGCAAT ACCCAGCTCG GAGTTTCCGC CCTC                 54

(2) INFORMATION FOR SEQ ID NO: 10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 10:

GCCCCGTGGC AGTAGTGAGC CACCACCTCC GGGGCCTTGT TCGCC                           45

(2) INFORMATION FOR SEQ ID NO: 11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 11:

GAACAAGGCC CCGGAGGTGG TGGCTCACTA GTGCCACGGG GCTCT                           45

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear

```
    (xi) SEQUENCE DESCRIPTION: SEQ ID NO: 12:

GTATTCTAGG CTTGCTCCGG GCAGA                                          25

(2) INFORMATION FOR SEQ ID NO: 13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 13:

TCACTGTGGA GTGGAGGGCA CAGTCCGAGT CTGCCCGGAG CAAGC                    45

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 14:

TTCCCGGGTC ATTTACCAGG GGAGCG                                         26
```

This has been a description of the present invention, along with a preferred method of practicing the present invention. However, the invention itself should only be defined by the appended claims wherein we claim:

1. A method for stimulating T cells in vivo, comprising administering in vivo an effective amount of a fusion protein to stimulate said T cells, said fusion protein comprising a plurality of MHC molecules complexed to an immunoglobulin constant domain, and a selected antigen associated with said plurality of MHC molecules, wherein said immunoglobulin constant domain includes a portion that can bind to an $F_c$ receptor, whereby said T cells are activated against said selected antigen.

2. The method of claim 1, wherein said immunoglobulin constant domain consists essentially of the CH3 domain.

3. The method of claim 2, wherein said immunoglobulin constant domain further comprises the CH2 domain and the hinge region.

* * * * *